United States Patent
Nakatake et al.

(10) Patent No.: US 10,774,321 B2
(45) Date of Patent: Sep. 15, 2020

(54) METHOD FOR MONOMERIZING MATRIX METALLOPROTEINASE 7 (MMP-7) AGGREGATE

(71) Applicant: KM BIOLOGICS CO., LTD., Kumamoto (JP)

(72) Inventors: Hiroshi Nakatake, Koshi (JP); Masaki Hirashima, Koshi (JP); Hideki Takeo, Kumamoto (JP); Reiko Matsuyama, Kumamoto (JP); Wataru Morikawa, Kumamoto (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 0 days.

(21) Appl. No.: 15/310,908

(22) PCT Filed: May 20, 2015

(86) PCT No.: PCT/JP2015/064451
§ 371 (c)(1),
(2) Date: Nov. 14, 2016

(87) PCT Pub. No.: WO2015/178414
PCT Pub. Date: Nov. 26, 2015

(65) Prior Publication Data
US 2017/0081654 A1    Mar. 23, 2017

(30) Foreign Application Priority Data

May 21, 2014  (JP) ................................. 2014-105452

(51) Int. Cl.
| | | |
|---|---|---|
| C12N 9/96 | (2006.01) | |
| A61K 47/02 | (2006.01) | |
| A61K 47/26 | (2006.01) | |
| A61K 47/10 | (2017.01) | |
| C12N 9/64 | (2006.01) | |
| A61K 47/16 | (2006.01) | |
| A61K 38/46 | (2006.01) | |
| A61K 38/48 | (2006.01) | |
| C12N 15/52 | (2006.01) | |

(52) U.S. Cl.
CPC ............... *C12N 9/96* (2013.01); *A61K 38/46* (2013.01); *A61K 38/4886* (2013.01); *A61K 47/02* (2013.01); *A61K 47/10* (2013.01); *A61K 47/16* (2013.01); *A61K 47/26* (2013.01); *C12N 9/64* (2013.01); *C12N 9/6491* (2013.01); *C12N 15/52* (2013.01); *C12Y 304/24023* (2013.01)

(58) Field of Classification Search
CPC ............... A61K 38/4886; A61K 47/02; A61K 2300/00; A61K 38/1709; C12N 9/6491; C12N 9/96; C12Y 304/24023
See application file for complete search history.

(56) References Cited

U.S. PATENT DOCUMENTS

| | | | |
|---|---|---|---|
| 6,010,893 A | 1/2000 | Kihira | |
| 6,194,189 B1 | 2/2001 | Senior | |
| 6,630,501 B1 * | 10/2003 | Dive | ....................... C07F 9/301 |
| | | | 514/16.6 |
| 2004/0243319 A1 | 12/2004 | Tickle et al. | |
| 2006/0099567 A1 | 5/2006 | Muller-Cohn et al. | |
| 2011/0262998 A1 | 10/2011 | Nakatake et al. | |
| 2012/0329128 A1 | 12/2012 | Hasslacher et al. | |
| 2013/0039898 A1 | 2/2013 | Okhamafe et al. | |

FOREIGN PATENT DOCUMENTS

| | | |
|---|---|---|
| EP | 1 593 391 | 8/2013 |
| JP | 10-276774 | 10/1998 |
| JP | 2938352 | 8/1999 |
| JP | 2000-226329 | 8/2000 |
| JP | 2000-344672 | 12/2000 |
| JP | 2002-173424 | 6/2002 |
| JP | 2005-6509 | 1/2005 |
| JP | 2005-528109 | 9/2005 |
| JP | 2008-206491 | 9/2008 |
| JP | 2009-517086 | 4/2009 |
| JP | 2013-518893 | 5/2013 |
| RU | 2295329 | 3/2005 |
| WO | 03/022244 | 3/2003 |

(Continued)

OTHER PUBLICATIONS

Leibly et al. Stabilizing additives added during cell lysis aid in the solubilization of recombinant proteins. PLoS One. 2012;7(12): e52482.*
Soler et al., "Zinc Content of Promatrilysin, Matrilysin and the Stromelysin Catalytic Domain", Biochemical and Biophysical Research Communications, 201(2):917-923 (1994).
Ii et al., "Role of Matrix Metalloproteinase-7 (Matrilysin) in Human Cancer Invasion, Apoptosis, Growth, and Angiogenesis" Exp. Biol. Med. (Maywood), 231:20-27 (2006).
Haro et al., "Up-Regulated Expression of Matrilysin and Neutrophil Collagenase in Human Herniated Discs", Journal of Spinal Disorders, 12(3):245-249, (1999).

(Continued)

*Primary Examiner* — Lynn Y Fan
(74) *Attorney, Agent, or Firm* — Wenderoth, Lind & Ponack, L.L.P.

(57) ABSTRACT

A method for monomerization of MMP-7 aggregates is provided. A method for monomerization of MMP-7 aggregates which comprises treating MMP-7 aggregates with a buffer solution comprising a monovalent cation chloride (sodium chloride, potassium chloride, etc.) at a low concentration or with a buffer solution not comprising a monovalent cation chloride, a process for preparing MMP-7 which involves said method for monomerization, and a (pharmaceutical) composition comprising MMP-7 in the aforementioned buffer solution. In case that a (pharmaceutical) composition comprising MMP-7 at a low concentration is prepared, the aforementioned buffer solution comprising sugar alcohols or sugars is used.

20 Claims, 5 Drawing Sheets
Specification includes a Sequence Listing.

(56) References Cited

FOREIGN PATENT DOCUMENTS

WO     2010/047347     4/2010
WO     2012/167271     12/2012

OTHER PUBLICATIONS

Haro et al., "Experimental studies on the effects of recombinant human matrix metalloproteinases on herniated disc tissues—how to facilitate the natural resorption process of herniated disc", Journal of Orthopedic Research, 23:412-419 (2005).
Miyazaki et al., "Purification and Characterization of Extracellular Matrix-degrading Metalloproteinase, Matrin (Pump-1), Secreted from Human Rectal Carcinoma Cell Line", Cancer Research, 50:7758-7764, (1990).
Barnett et al., "Production, Purification, and Characterization of Human Matrilysin (PUMP) from Recombinant Chinese Hamster Ovary Cells", Protein Expression and Purification, 5(1):27-36 (1994).
Crabbe et al., "Biochemical Characterization of Matrilysin. Activation Conforms to the Stepwise Mechanisms Proposed for Other Matrix Metalloproteinases", Biochemistry, 31(36):8500-8507 (1992).
Oneda et al., "Refolding and Recovery of Recombinant Human Matrix Metalloproteinase 7 (Matrilysin) from Inclusion Bodies Expressed by *Escherichia coli*", J. Biochem., 126:905-911 (1999).
Browner et al., "Matrilysin—Inhibitor Complexes: Common Themes among Metalloproteinases", Biochemistry, 34(20):6602-6610, (1995).
López De Turiso et al., "Expression and purification of human matrilysin produced in baculovirus-infected insect cells", Journal of Biotechnology, 46(3):235-241 (1996).
Haro, "Translational research of herniated discs: current status of diagnosis and treatment", J. Orthop. Sci., 19(4):515-520 (2014).
Ou et al., "The expression and refolding of isotopically labeled recombinant Matrilysin for NMR studies", Protein Expression and Purification, 47(2):367-373 (2006).
Kannan et al., "Purification of Active Matrix Metalloproteinase Catalytic Domains and Its Use for Screening of Specific Stromelysin-3 Inhibitors", Protein Expression and Purification, 16(1):76-83 (1999).
Kihira et al., "Production of Recombinant Human Matrix Metalloproteinase 7 (Matrilysin) with Potential Role in Tumor Invasion by Refolding from *Escherichia coli* Inclusion Bodies and Development of Sandwich ELISA of MMP-7", Urol. Oncol., 2(1):20-26 (1996).
Zhou et al., "Autoantibodies against MMP-7 as a novel diagnostic biomarker in esophageal squamous cell carcinoma", World Journal of Gastroenterology, 17(10):1373 -1378 (2011).
Inouye et al., "States of Tryptophyl Residues and Stability of Recombinant Human Matrix Metalloproteinase 7 (Matrilysin) as Examined by Fluorescence", J. Biochem., 128(3):363-369 (2000).
Samukange et al., "Effects of heparin and cholesterol sulfate on the activity and stability of human matrix metalloproteinase 7", Bioscience, Biotechnology, and Biochemistry, 78(1):41-48.
Written Opinion dated Aug. 18, 2015 in corresponding International Application No. PCT/JP2015/064451.
International Search Report dated Aug. 18, 2015 in corresponding International Application No. PCT/JP2015/064451.
Extended European Search Report dated Nov. 7, 2017 in corresponding European patent application No. 15795955.2.
Yu W-H et al., "Heparan Sulfate Proteoglycans as Extracellular Docking Molecules for Matrilysin (Matrix Metalloproteinase 7*", Journal of Biological Chemistry, vol. 275, No. 6, 2000, pp. 4183-4191.
Office Action dated Oct. 1, 2019 in corresponding Japanese Patent Application No. 2016-521126, with machine English translation, 10 pages.
Official Action dated Aug. 13, 2019 in corresponding Russian Patent Application No. 2016150091, with English Translation.
Official Action dated Aug. 27, 2019 in corresponding Chinese Patent Application No. 201580039303.7, with Machine English Translation.
Communication pursuant to Article 94(3) EPC dated Aug. 6, 2019 in corresponding European Patent Application No. 15795955.2.
Official Action Record of Negotiations dated Dec. 24, 2019 in corresponding Russian Patent Application No. 2016150091, with English Translation.
Decision of Refusal dated Apr. 7, 2020 in corresponding Japanese Patent Application No. 2016-521126 with English-language translation.
Office Action dated Mar. 19, 2020 in corresponding Indian Patent Application No. 201647042929 with English-language.

* cited by examiner

SEQUENCE LISTING

<160> NUMBER OF SEQ ID NOS: 9

<210> SEQ ID NO 1
<211> LENGTH: 27
<212> TYPE: DNA
<213> ORGANISM: Artificial
<220> FEATURE:
<223> OTHER INFORMATION: Primer used for the cloning of a pro-matrix
      metalloproteinase-7 gene

<400> SEQUENCE: 1
ccataggtcc aagaacaatt gtctctg                                        27

<210> SEQ ID NO 2
<211> LENGTH: 26
<212> TYPE: DNA
<213> ORGANISM: Artificial
<220> FEATURE:
<223> OTHER INFORMATION: Primer used for the cloning of a pro-matrix
      metalloproteinase-7 gene

<400> SEQUENCE: 2
caatccaatg aatgaatgaa tggatg                                         26

<210> SEQ ID NO 3
<211> LENGTH: 81
<212> TYPE: DNA
<213> ORGANISM: Artificial
<220> FEATURE:
<223> OTHER INFORMATION: Primer used to obtain a DNA fragment consisting
      of an alkaline phosphatase signal peptide and a pro-matrix
      metalloproteinase-7

<400> SEQUENCE: 3
catatgaaac aaagcactat tgcactggca ctcttaccgt tactgtttac ccctgtgacc     60
aaggccctgc cgctgcctca g                                              81

<210> SEQ ID NO 4
<211> LENGTH: 26
<212> TYPE: DNA
<213> ORGANISM: Artificial
<220> FEATURE:
<223> OTHER INFORMATION: Primer used to obtain a DNA fragment consisting
      of an alkaline phosphatase signal peptide and a pro-matrix
      metalloproteinase-7

<400> SEQUENCE: 4
ggatccctat ttctttcttg aattac                                         26

<210> SEQ ID NO 5
<211> LENGTH: 35
<212> TYPE: DNA
<213> ORGANISM: Artificial
<220> FEATURE:

-continued

<223> OTHER INFORMATION: Primer used to obtain a DNA fragment consisting
      of a modified alkaline phosphatase signal peptide and a pro-matrix
      metalloproteinase-7

<400> SEQUENCE: 5
ctgtttaccc ctgtgaccaa ggaactgccg ctgcc                                35

<210> SEQ ID NO 6
<211> LENGTH: 33
<212> TYPE: DNA
<213> ORGANISM: Artificial
<220> FEATURE:
<223> OTHER INFORMATION: Primer used to obtain a DNA fragment consisting
      of a modified alkaline phosphatase signal peptide and a pro-matrix
      metalloproteinase-7

<400> SEQUENCE: 6
cttggtcaca ggggtaaaca gtggcggtaa gag                                  33

<210> SEQ ID NO 7
<211> LENGTH: 7
<212> TYPE: PRT
<213> ORGANISM: Artificial
<220> FEATURE:
<223> OTHER INFORMATION: A DNP-protein of fluorescent substrate used for
      measuring the activity of MMP-7

<400> SEQUENCE: 7

Pro Leu Gly Leu Trp Ala Arg
1               5

<210> SEQ ID NO 8
<211> LENGTH: 21
<212> TYPE: PRT
<213> ORGANISM: Artificial
<220> FEATURE:
<223> OTHER INFORMATION: Amino acid sequence of a signal peptide of
      alkaline phosphatase

<400> SEQUENCE: 8

Met Lys Gln Ser Thr Ile Ala Leu Ala Leu Leu Pro Leu Leu Phe Thr
1               5                   10                  15

Pro Val Thr Lys Ala
            20

<210> SEQ ID NO 9
<211> LENGTH: 7
<212> TYPE: PRT
<213> ORGANISM: Artificial
<220> FEATURE:
<223> OTHER INFORMATION: A MOCAc-protein of fluorescent substrate used
      for measuring the activity of MMP-7
<220> FEATURE:
<221> NAME/KEY: misc_feature
<222> LOCATION: (5)..(5)
<223> OTHER INFORMATION: Xaa=Nbeta-(2,4-dinitrophenyl)-L-2,3-
      diaminopropionyl

<400> SEQUENCE: 9

Pro Leu Gly Leu Xaa Ala Arg
1               5

METHOD FOR MONOMERIZING MATRIX METALLOPROTEINASE 7 (MMP-7) AGGREGATE

TECHNICAL FIELD

The present invention relates to a method for monomerizing aggregates of matrix metalloproteinase 7 (hereinafter also referred to as "MMP-7"). Specifically, the present invention relates to a method for monomerizing MMP-7 aggregates which comprises treating MMP-7 aggregates with a solution comprising a low concentration of a monovalent cation compound or with a solution not comprising said compound, a process for preparing MMP-7 which involves said method for monomerizing MMP-7 aggregates, and a (pharmaceutical) composition comprising MMP-7 in the aforementioned solution where sugar alcohols or sugars are further dissolved.

BACKGROUND ART

MMP-7 is one of matrix metalloproteinases (hereinafter also referred to as "MMP") belonging to a zinc metalloproteinase family which possesses a zinc molecule at the active site (cf. for instance, Non-patent reference 1). MMP is produced as a precursor, its signal sequence is processed upon extracellular secretion, and then a pro-sequence is processed to yield an active form. MMP extracellularly secreted controls metabolism of extracellular matrix. On the other hand, it is reported that MMP-7 is mainly secreted from cancer cells and is involved in invasion and metastasis (cf. for instance, Non-patent reference 2). MMP-7 lacks the hinge region and the hemopexin-like domain common in many of the other MMPs and consists of the minimum molecular unit as compared to the other MMPs. A substrate of MMP-7 is components constituting collagen or extracellular matrix (fibronectin, vitronectin, laminin, aggrecan).

MMP-7 is presumed to be involved in spontaneous remission of nucleus pulposus existing in the (spinal) epidural space viewing that a substrate of MMP-7 is aggrecan which is a main component of the cartilage tissue and that macrophages from specimen of intervertebral disk displacement surgery express MMP-7 (cf. for instance, Non-patent reference 3). Thereafter, Haro et al. administered MMP-7 to the intervertebral disk of hernial dog and observed the decrease in a volume of nucleus pulposus within the intervertebral disk to thereby show the possibility of MMP-7 as a medicament for treating intervertebral disk displacement (cf. for instance, Non-patent reference 4). Development of MMP-7 as a medicine is desired. However, MMP-7 occurs in the living body only in a trace amount and thus it is extremely difficult to isolate and purify MMP-7 from the living body. Besides, when components from the living body are used, there is a concern in view of safety such as potential viral infection. Although MMP-7 can be obtained from cancer cells, it is not preferable to use cancer cells as a source for production (cf. for instance, Non-patent reference 5).

For dissolving such problems, an attempt has been made to obtain MMP-7 by a recombinant DNA technology. There are the report by Barnett et al. that MMP-7 is expressed in CHO cells (cf. for instance, Non-patent reference 6), the report that, by using a nucleic acid fragment generated by linking a nucleotide sequence of a signal sequence of alkaline phosphatase to a gene sequence of pro-matrix metalloproteinase 7 (hereinafter also referred to as "proMMP-7") optimized for codon usage of E. coli, soluble proMMP-7 was expressed at 34° C. and insoluble proMMP-7 was expressed at 42° C. (cf. for instance, Patent reference 1) and the report that, by using a nucleic acid fragment generated by linking a modified signal peptide to a gene fragment of proMMP-7, proMMP-7 is expressed as an inclusion body in a large amount (cf. for instance, Patent reference 2).

For conversion of proMMP-7 to active MMP-7, it is reported that proMMP-7 is heated at 37° C. in the presence of 1 mM (4-aminophenyl)mercuric acetate (APMA) or 0.2 µM trypsin or a solution containing proMMP-7 is heated at 53° C. (cf. for instance, Non-patent reference 7). They revealed that, after a low concentration (less than 1 mg/ml) of activated MMP-7 (also known as Matrilysin) was stored at −20° C. for 6 months and at room temperature for 28 days, there was no change in its activity and behavior on electrophoresis. Although there is no definite description about the change, they appear to suggest that no decomposition of Matrilysin was observed from the results of electrophoresis. In addition to these, there are various reports on purification of proMMP-7 and MMP-7 such as Kihira, and Oneda et al. (cf. for instance, Patent reference 1, Non-patent reference 8) and thus a method for the purification of MMP-7 has been established to some extent at an experimental level. In general, a method for the purification of MMP-7 at an experimental level is scaled up for large-scale production. However, a method for the manufacture of MMP-7 in a large amount has never been established. There is little report on the problems in the manufacture of MMP-7 in a large amount and solution therefor.

For a composition comprising MMP-7, that which comprises tris(hydroxymethyl)aminomethane hydrochloride (Tris hydrochloride), calcium chloride and sodium chloride is reported (cf. for instance, Patent references 3 to 5, Non-patent references 7, 9). It is known that metalloproteinase such as MMP-7, in a state of a solution composition, is stabilized in the coexistence of calcium chloride and sodium chloride (cf. for instance, Patent reference 6). In particular, a medicine is normally required to have an osmotic pressure of around that of body fluid in view of safety. Sodium chloride is commonly used as an osmotic pressure regulator of a liquid composition. As a practical matter, most of the compositions disclosed in these documents comprise a monovalent cation compound such as sodium chloride at the concentration isotonic to or more than that of body fluid. Besides, the compositions disclosed in these documents do not comprise sugar alcohols or sugars.

PATENT REFERENCES

Patent reference 1: JP patent 2938352
Patent reference 2: WO 2010/047347A1
Patent reference 3: JP 2000-344672
Patent reference 4: JP 2000-226329
Patent reference 5: JP 2002-173424
Patent reference 6: JP 2005-6509

NON-PATENT REFERENCES

Non-patent reference 1: Soler et al., Biochem Biophys Res Commun, 1994, vol. 201, p. 917-923
Non-patent reference 2: Ii et al., Exp Biol Med (Maywood), 2006, vol. 231, p. 20-27
Non-patent reference 3: Haro et al., J Spinal Disord, 1999, vol. 12, p. 245-249
Non-patent reference 4: Haro et al., J Orthop Res, 2005, vol. 23, p. 412-419

Non-patent reference 5: Miyazaki et al., Cancer Research, 1990, vol. 50, p. 7758-7764

Non-patent reference 6: Barnett et al., Protein Exp Purif, 1994, vol. 5, p. 27-36

Non-patent reference 7: Crabbe et al., Biochemistry, 1992, vol. 31, p. 8500-8507

Non-patent reference 8: Oneda et al., J Biochem, 1999, vol. 126, p. 905-911

Non-patent reference 9: Browner et al., Biochemistry, 1995, vol. 34, p. 6602-6610

DISCLOSURE OF THE INVENTION

Technical Problem to be Solved by the Invention

In the course of developing a medicine comprising MMP-7, the present inventors have found MMP-7 forms aggregates under the circumstances where a monovalent cation compound such as sodium chloride is at 150 mM or more which is isotonic to that of body fluid, like in case of the conventional medicinal products, especially a liquid composition of metalloproteinase as described above and that MMP-7 is adsorbed to gel in an apparatus normally used the manufacture of proteins or their preparations or to a container such as a vial normally used for storage of preparations. Thus, the problem was to provide a method for monomerizing MMP-7 aggregates where adsorption of MMP-7 to a manufacturing apparatus is suppressed at the time when MMP-7 is manufactured, a process for preparing MMP-7 which involves said method for monomerizing MMP-7 aggregates, and a (pharmaceutical) composition comprising MMP-7 where aggregate formation and adsorption of MMP-7 is suppressed.

Means for Solving the Problems

The present inventors have earnestly investigated in order to solve the above problems and as a result have found the following (1) to (4) to complete the present invention.

(1) MMP-7 aggregates are dissociated to form monomers by the treatment with a solution such as a Tris buffer (pH 6 to 8) comprising a low concentration of a monovalent cation chloride (sodium chloride and potassium chloride). Also, MMP-7 aggregates likewise form monomers when they are treated with the solution not comprising a monovalent cation chloride.

(2) By incorporating a method for monomerizing MMP-7 aggregates with the treatment as mentioned above (hereinafter also simply referred to as "a method for monomerization") into a manufacturing process of MMP-7, efficiency in producing MMP-7 can be increased. In particular, by incorporating the method for monomerization into a process of treatment with ultrafiltration membrane immediately after conversion of proMMP-7 into MMP-7 through self-activation, more significant effects can be obtained.

(3) MMP-7 monomers maintain a high enzymatic activity.

(4) By adding sugars or sugar alcohols such as mannitol and sucrose to the Tris buffer as mentioned above, not only formation of MMP-7 aggregates is suppressed but also adsorption of MMP-7 to gel and the wall of a vial is suppressed. Namely, by preparing a composition comprising a monovalent cation chloride at a concentration of around 150 mM which is isotonic to that of body fluid or less when made to an aqueous solution and sugar alcohols or sugars, the resulting solution becomes a pharmaceutical preparation where formation of MMP-7 aggregates and adsorption of MMP-7 are suppressed.

Accordingly, the present invention encompasses a method for monomerizing MMP-7 aggregates (method for monomerization), a process for preparing MMP-7 which involves said method for monomerization and a (pharmaceutical) composition comprising MMP-7 prepared by using the aforementioned buffer and relates to the followings:

[1] A method for monomerization of matrix metalloproteinase 7 (MMP-7) aggregates which comprises treating MMP-7 aggregates with a solution comprising a monovalent cation compound at 130 mM or less or with a solution not comprising a monovalent cation compound.

[2] The method for monomerization according to [1] wherein the MMP-7 aggregates are treated with a solution comprising a monovalent cation compound at 130 mM or less.

[3] The method for monomerization according to [1] wherein the MMP-7 aggregates are treated with a solution not comprising a monovalent cation compound.

[4] The method for monomerization according to [1] or [2] wherein the monovalent cation compound is at 100 mM or less.

[5] The method for monomerization according to [1], [2] or [4] wherein the monovalent cation compound is at 80 mM or less.

[6] The method for monomerization according to [1], [2], [4] or [5] wherein the monovalent cation compound is at 40 mM or less.

[7] The method for monomerization according to [1], [2], [4], [5] or [6] wherein the monovalent cation compound is selected from the group consisting of sodium chloride, potassium chloride, sodium sulfate, potassium sulfate, sodium carbonate, potassium carbonate, sodium phosphate and potassium phosphate.

[8] The method for monomerization according to [1], [2], [4], [5] or [6] wherein the monovalent cation compound is from a monovalent cation chloride.

[9] The method for monomerization according to [8] wherein the monovalent cation compound is selected from the group consisting of sodium chloride and potassium chloride.

[10] The method for monomerization according to any one of [1] to [9] wherein the solution further comprises calcium chloride.

[11] The method for monomerization according to [10] wherein the calcium chloride is at 30 mM or less.

[12] The method for monomerization according to any one of [1] to [11] wherein the solution is a buffer solution.

[13] The method for monomerization according to [12] wherein the buffer solution is 5 to 25 mM Tris buffer.

[14] The method for monomerization according to any one of [1] to [13] wherein the MMP-7 is at 20 mg/ml or less.

[15] The method for monomerization according to [13] or [14] wherein the solution is 5 to 25 mM Tris buffer (pH 6 to 8) comprising 30 to 40 mM sodium chloride and 5 to 30 mM calcium chloride.

[16] The method for monomerization according to any one of [1] to [15] wherein the solution further comprises sugar alcohols and/or sugars.

[17] The method for monomerization according to [16] wherein the sugar alcohols and/or sugars are selected from the group consisting of sucrose, lactose, maltose, xylose, trehalose, mannitol, sorbitol, xylitol, maltitol, lactitol, and oligosaccharide alcohols.

[18] The method for monomerization according to [16] or [17] wherein the sugar alcohols and/or sugars are at 2% or more.
[19] The method for monomerization according to [18] wherein the sugar alcohols and/or sugars are at 2 to 7%
[20] The method for monomerization according to any one of [17] to [19] wherein the sugar alcohols and/or sugars are mannitol or sucrose.
[21] The method for monomerization according to [20] wherein the mannitol is at 2 to 5% and the sucrose is at 2 to 7%.
[22] A process for preparation of MMP-7 which comprises a step consisting of the method for monomerization as set forth in any one of [1] to [21].
[23] The process for preparation according to [22] wherein the step is carried out after a step of treatment using a solution comprising a monovalent cation compound at 130 mM or more.
[24] The process for preparation according to [22] or [23] wherein the process comprises the following steps (1) to (5):
(1) a step of disrupting cells producing proMMP-7 inclusion body;
(2) a step of dissolution/refolding treatment of proMMP-7 inclusion body;
(3) a step of purification of proMMP-7;
(4) a step of self-activation of proMMP-7 into MMP-7; and
(5) a step consisting of the method for monomerization as set forth in any one of [1] to [21].
[25] The process for preparation according to [24] wherein the step (5) is a step of concentration using ultrafiltration membrane.
[26] A (pharmaceutical) composition comprising matrix metalloproteinase 7 (MMP-7) as an active ingredient in a solution comprising a monovalent cation compound at 130 mM or less or in a solution not comprising a monovalent cation compound.
[27] The (pharmaceutical) composition comprising MMP-7 according to [26] wherein the composition comprises MMP-7 as an active ingredient in a solution comprising a monovalent cation compound at 130 mM or less.
[28] The (pharmaceutical) composition comprising MMP-7 according to [26] wherein the composition comprises MMP-7 as an active ingredient in a solution not comprising a monovalent cation compound.
[29] The (pharmaceutical) composition comprising MMP-7 according to [26] or [27] wherein the monovalent cation compound is selected from the group consisting of sodium chloride, potassium chloride, sodium sulfate, potassium sulfate, sodium carbonate, potassium carbonate, sodium phosphate and potassium phosphate.
[30] The (pharmaceutical) composition comprising MMP-7 according to [26] or [27] wherein the monovalent cation compound is from a monovalent cation chloride.
[31] The (pharmaceutical) composition comprising MMP-7 according to [30] wherein the monovalent cation compound is selected from the group consisting of sodium chloride and potassium chloride.
[32] The (pharmaceutical) composition comprising MMP-7 according to any one of [26] to [31] wherein the composition further comprises calcium chloride.
[33] The (pharmaceutical) composition comprising MMP-7 according to [32] wherein the calcium chloride is at 30 mM or less.
[34] The (pharmaceutical) composition comprising MMP-7 according to any one of [26] to [33] wherein the solution is a buffer solution.
[35] The (pharmaceutical) composition comprising MMP-7 according to [34] wherein the buffer solution is 5 to 25 mM Tris buffer.
[36] The (pharmaceutical) composition comprising MMP-7 according to any one of [26] to [35] wherein the MMP-7 is at 20 mg/ml or less.
[37] The (pharmaceutical) composition comprising MMP-7 according to [36] wherein the MMP-7 is at 1 µg/ml to 1 mg/ml.
[38] The (pharmaceutical) composition comprising MMP-7 according to [35], [36] or [37] wherein the solution is 5 to 25 mM Tris buffer (pH 6 to 8) comprising 30 to 40 mM sodium chloride and 5 to 30 mM calcium chloride.
[39] The (pharmaceutical) composition comprising MMP-7 according to any one of [26] to [38] wherein the solution further comprises sugar alcohols and/or sugars.
[40] The (pharmaceutical) composition comprising MMP-7 according to [39] wherein the sugar alcohols and/or sugars are selected from the group consisting of sucrose, lactose, maltose, xylose, trehalose, mannitol, sorbitol, xylitol, maltitol, lactitol, and oligosaccharide alcohols.
[41] The (pharmaceutical) composition comprising MMP-7 according to [39] or [40] wherein the sugar alcohols and/or sugars are at 2% or more.
[42] The (pharmaceutical) composition comprising MMP-7 according to [41] wherein the sugar alcohols and/or sugars are at 2 to 7%.
[43] The (pharmaceutical) composition comprising MMP-7 according to any one of [40] to [42] wherein the sugar alcohols and/or sugars are mannitol or sucrose.
[44] The (pharmaceutical) composition comprising MMP-7 according to [43] wherein the mannitol is at 2 to 5% and the sucrose is at 2 to 7%.
[45] A solid (pharmaceutical) composition comprising MMP-7 wherein the composition can be dissolved in a solvent and the composition upon dissolution is the composition as set forth in any one of [26] to [44].
[46] A medicament for treating intervertebral disk displacement which comprises the (pharmaceutical) composition comprising MMP-7 as set forth in any one of [26] to [45].

Effects of the Invention

In accordance with the present invention, a method for monomerization of MMP-7 aggregates with ease is provided. Thus, by incorporating the method into manufacturing process of MMP-7, productivity and recovery efficiency of MMP-7 can be increased.

Besides, MMP-7 as monomerized by the method has a higher specific activity of an enzyme as compared to MMP-7 aggregates and thus can be a suitable material for providing a MMP-7 preparation of high quality.

Furthermore, as an embodiment of the present invention, by storing MMP-7 in a buffer comprising sodium chloride at a low concentration and sugar alcohols or sugars, MMP-7 not only maintains its monomeric form but also a high enzymatic activity, and also adsorption of MMP-7 to a storage container can be suppressed. Therefore, the buffer used in a method for monomerization of the present invention is useful as a preservative solution of a MMP-7 preparation. The MMP-7 composition of the present invention, which comprises sodium chloride at a low concentration when made to an aqueous solution and sugar alcohols or sugars, is useful as a liquid composition for medicinal use and a composition for preparing the same where the formation of MMP-7 aggregates is suppressed and adsorption of MMP-7 to a container is suppressed.

BEST MODE FOR CARRYING OUT THE INVENTION

Figure 1:
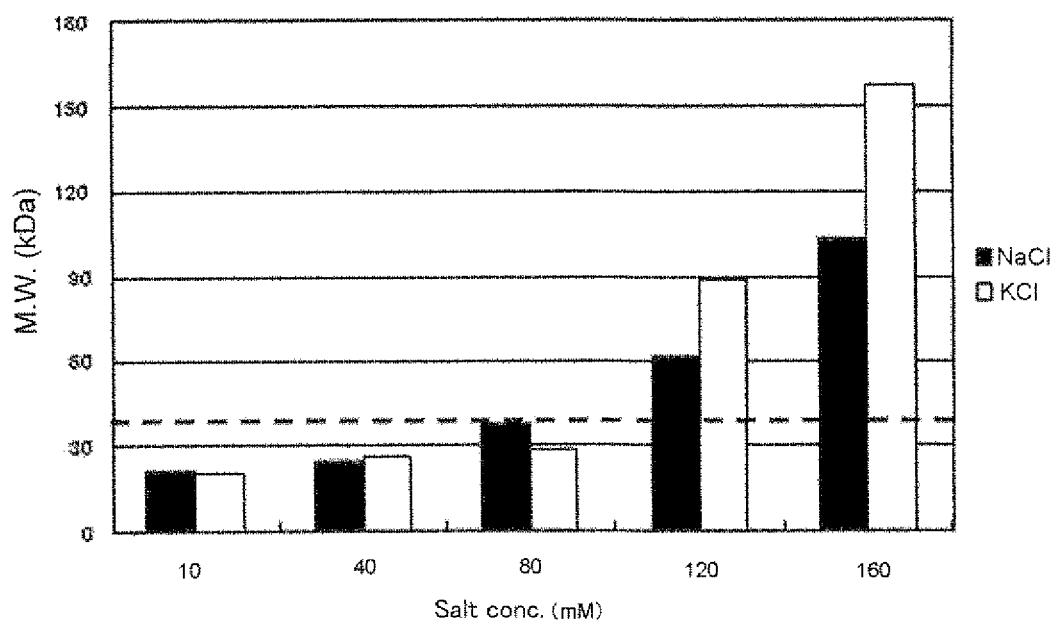
FIG. 1 shows the suppressive effects of sodium chloride (NaCl) and potassium chloride (KCl) to MMP-7 aggregate formation based on the analysis of molecular weight of MMP-7 measured by dynamic light scattering.

The present invention provides a method for monomerization of MMP-7 aggregates, a process for preparing MMP-7 which involves said method for monomerization and a (pharmaceutical) composition comprising MMP-7. The present invention is characterized by that MMP-7 aggregates are treated with a solution comprising a low concentration of a monovalent cation compound and further comprising sugar alcohols or sugars (hereinafter also referred to as "a solution for monomerization"), that MMP-7 is stored in said solution and that an MMP-7 composition comprises a low concentration of a monovalent cation compound and sugar alcohols or sugars when made to an aqueous solution.

Detection of MMP-7 aggregates is carried out by measuring a molecular weight of MMP-7 by dynamic light scattering, size exclusion chromatography, ultra-centrifugation and the like and comparing the measured weight with the molecular weight of monomeric MMP-7 (about 19 kDa) calculated from the amino acid sequence. For the present invention, MMP-7 was determined to be monomeric in case that the molecular weight of MMP-7 in a sample is between a range of from 19 kDa to 38 kDa whereas MMP-7 was determined to form aggregates in case that it is 38 kDa or more. The above criteria of determination are made by taking into consideration trueness of measurement by dynamic light scattering such that MMP-7 evidently formed aggregates when the molecular weight is more than that of a dimer whereas MMP-7 is monomeric when it is less than that of a dimer.

Monomerization of MMP-7 is carried out by treating MMP-7 aggregates with a solution for monomerization. As used herein, "treating MMP-7 aggregates with a solution for monomerization" means that MMP-7 aggregates are exposed to a solution for monomerization and includes dissolution in said solution and includes that, when MMP-7 aggregates are dissolved in a solution containing a monovalent cation compound at a high concentration of 130 mM or more, exchange of buffer is conducted with ultrafiltration membrane or dialysis membrane using a solution for monomerization. For a buffer to keep the pH of the solution for monomerization constant, it is possible to use Tris buffer, phosphate buffer, glycine buffer and carbonic acid buffer, among which a suitable buffer may be selected depending on the pH at the monomerization treatment. A concentration of a buffer may be in a range of 5 to 25 mM, preferably 5 to 20 mM. The pH may be in a range of 5 to 9, preferably 6 to 8. More preferably, a Tris buffer is selected that exerts an effect on improvement of stability of metalloproteinase with the Tris buffer having a concentration of 5 to 10 mM and pH of 6 to 8 (cf. JP 2011-521906).

As used herein, "a monovalent cation compound" means a compound consisting of a monovalent cation and a counterpart anion, including sodium chloride, potassium chloride, sodium sulfate, potassium sulfate, sodium carbonate, potassium carbonate, sodium phosphate, potassium phosphate and the like. Also, as used herein, "a monovalent cation chloride" means a compound consisting of a monovalent cation and a chloride ion. For a monovalent cation compound as used herein, any monovalent cation compound may be used but preferably a monovalent cation chloride is used. Specifically, sodium chloride and potassium chloride, preferably sodium chloride is used.

For dissociating MMP-7 aggregates into monomeric MMP-7, a low concentration of a monovalent cation compound is used. MMP-7 dissociated into monomers is maintained as monomers in a solution for monomerization comprising a low concentration of a monovalent cation compound. The same effect can be obtained by using a solution for monomerization or water not comprising a monovalent cation compound. Therefore, the present invention encompasses a method for monomerization of MMP-7 aggregates using a solution for monomerization, which solution includes liquid such as water in accordance with the present invention, not comprising a monovalent cation compound. Hereinafter, a solution comprising a low concentration of a monovalent cation compound and the solution not comprising a monovalent cation compound are also collectively referred to as merely "a solution for monomerization".

By adding a polyvalent cation compound to a solution for monomerization, a range of a concentration of a monovalent cation compound to be treated can be broadened. A polyvalent cation compound is preferably a divalent cation compound, more preferably a divalent calcium ion compound, and most preferably calcium chloride. Like a monovalent cation compound, "a polyvalent cation compound" means a compound consisting of a polyvalent cation and a counterpart anion.

Specifically, in case that water is used as a solution for monomerization, a monovalent cation compound at 40 mM or less is used and, by adding calcium chloride to a solution for monomerization, treatment with a solution for monomerization comprising a monovalent cation compound at more than 40 mM becomes possible. More specifically, a solution for monomerization comprising a monovalent cation compound at 80 mM or less when it comprises 5 mM to 10 mM calcium chloride, the solution comprising a monovalent cation compound at 100 mM or less when it comprises 10 mM to 30 mM calcium chloride, and the solution comprising a monovalent cation compound at 130 mM or less when it comprises 30 mM calcium chloride, can be used. This result demonstrates that, by the addition of calcium chloride, the effect of dissociation of MMP-7 aggregates into monomers and the suppressive effect to MMP-7 aggregate formation were enhanced. Besides, it can be seen from the results of Example 2 (FIG. 2) that this effect is proportional to a concentration of calcium chloride. Namely, by using a higher concentration of calcium chloride, higher effects of monomerization of MMP-7 and maintenance of MMP-7 monomers can be expected. From the above, a concentration of a monovalent cation compound is 130 mM or less, preferably 100 mM or less, more preferably 80 mM or less, and most preferably 40 mM or less, in case of an aqueous solution. Although a solution for monomerization may not comprise a monovalent cation compound, the solution comprising a monovalent cation compound is preferable in view of quality a pharmaceutical composition.

In accordance with the present invention, a solution for monomerization consisting of 5 to 25 mM Tris buffer (pH 6 to 8) comprising 30 to 40 mM sodium chloride and 5 to 30 mM calcium chloride, or the solution for monomerization without sodium chloride, may preferably be used.

A method for monomerization of MMP-7 aggregates of the present invention can be incorporated into a manufacturing process of MMP-7 so as to efficiently produce MMP-7 monomers of high quality. A general process for producing MMP-7 by a recombinant DNA technology is carried out by the steps of culture of cells, release of inclusion bodies, dissolution and refolding of inclusion bodies, purification of proMMP-7, conversion of proMMP-7 into MMP-7 by self-activation, purification and concentration of MMP-7.

More specifically, a method for monomerization of MMP-7 aggregates of the present invention is used in a manufacturing process of MMP-7 as described below. Firstly, E. coli producing proMMP-7 is prepared. In general, it can be prepared by introducing proMMP-7 gene inserted in an expression vector into E. coli by the ordinary procedure. However, since proMMP-7 has a potent toxicity against E. coli, productivity could be decreased drastically. In order to solve this problem, addition of a signal peptide at the N-terminus of proMMP-7 is devised. However, in case of proMMP-7, phenomena are observed that an expression level of proMMP-7 is not increased merely by adding a signal peptide and a portion of proMMP-7 expressed is decomposed. Such phenomena can be an obstacle to establishment of a process for efficient production of MMP-7. Therefore, as a starting material for production of MMP-7, it is preferable to use E. coli producing proMMP-7 which has an increased expression level of proMMP-7 and increased suppression of proMMP-7 decomposition by proteases. Such E. coli producing proMMP-7 can be prepared by the method described in WO2010/047347 (more specifically, cf. Preparation therein).

The thus obtained E. coli producing proMMP-7, after purification by repeating cloning, is preserved as a working cell bank and used as a seed for a large-scale culture for production of MMP-7 preparation. A working cell bank may be preserved under conditions normally used for preservation of recombinant E. coli, e.g. in a solution containing 7 to 10% dimethyl sulfoxide or 10 to 50% glycerol in a freezer at −80° to −20° C. or in liquid nitrogen or lyophilized in an ample to be preserved in a refrigerator at 2 to 10° C.

Cultivation of E. coli producing proMMP-7 on a production scale is carried out in two stages, i.e. preculture on a small scale and main culture on a large scale. For preculture, LB medium commonly used for recombinant E. coli, optionally supplemented with antibiotics such as ampicillin for retention of plasmid, may be used for propagation of E. coli producing proMMP-7. However, for main culture, a culture medium where substance causative of side effects is removed as much as possible is preferably used. Such culture medium includes, for instance, a glucose medium containing various trace metals such as magnesium, calcium, copper and sodium, LB medium, M9 medium and the like. Culture conditions may be those suited for propagation of E. coli, for instance, culture conditions of pH (pH 6 to 8), temperature (30° to 45° C.) and time (4 to 16 hours). These culture conditions may suitably be adjusted depending on a culture scale and treatment for induction of expression. An expression inducer is used for efficient expression of proMMP-7 and includes isopropyl-β-thiogalactopyranoside (IPTG), lactose and the like.

For recovery of MMP-7 from E. coli producing proMMP-7 cultured and propagated in a large amount after main culture, the procedures described below are carried out. Firstly, E. coli producing proMMP-7 is cultured and the propagated cells are disrupted by a suitable measure so as to release inclusion bodies consisting of proMMP-7 out of the cells. For disruption of cells, lysis with chemical substance (e.g. EDTA as a chelating agent), surfactant (e.g. Triton X100) and enzyme (e.g. lysozyme) or physical treatment with French press, sonication and the like may be used. By combining several of these procedures, cells can be disrupted more efficiently. A solution obtained after disruption of cells including inclusion bodies is subject to fractionation with ultrafiltration membrane or centrifuge for repetition of concentration and washing to remove most of cell components. For washing, a buffer commonly used such as Tris buffer, phosphate buffer, glycine buffer, carbonic acid buffer may be used. For a pore size of ultrafiltration membrane and the conditions of centrifuge, there are many reports which may be referred to. In case of treatment in a large amount, inclusion bodies are preferably recovered by fractionation with ultrafiltration membrane.

The recovered inclusion bodies are temporarily dissolved in a solution containing a reducing agent and a denaturing agent. For such reducing agent, cysteine, glutathione, dithiothreitol, 2-mercaptoethanol and the like may be used. Several of these may be used in combination. A concentration of a reducing agent may depend on an amount of inclusion bodies to be dissolved and may be in a range of 10 to 200 mM. For a denaturing agent, urea, guanidine hydrochloride and the like may be used. Urea and guanidine hydrochloride may be used at a concentration of 4 to 8M and 2 to 6M, respectively. For a buffer, one that is used for recovery of inclusion bodies such as, for instance, phosphate buffer and Tris buffer (pH 7.0 to 9) may be used. Temperature while dissolution is not particularly limited provided that it is 40° C. or lower. Dissolution time may be set seeing the conditions of dissolution of inclusion bodies. Normally, the solution is stirred for 30 minutes to 1 hour.

Next, refolding of proMMP-7, i.e. construction of normal steric structure, is performed by adding a refolding buffer containing a surfactant and metal ions to the solution of inclusion bodies. Brij 35 as surfactant and zinc acetate or cobalt chloride as metal ions are used at a concentration of 0.5 to 2% and 0.05 mM to 0.2 mM, respectively. A kind and a concentration of a buffer used for refolding may be the same as those used when inclusion bodies are dissolved. Refolding treatment is carried out by having the solution left to stand for a day or more.

For purification of proMMP-7 from the refolding solution, purification procedures commonly used in protein chemistry such as centrifuge, salting-out, ultrafiltration, isoelectric precipitation, electrophoresis, ion exchange chromatography, gel filtration chromatography, affinity chromatography, hydrophobic chromatography, hydroxyapatite chromatography and the like may be used in combination. proMMP-7 in the present invention can be purified by the steps consisting of ion exchange chromatography, hydrophobic chromatography and treatment with ultrafiltration membrane. Both chromatographies may be done in an ordinary manner. An amount of the obtained proteins and polypeptides may be measured with a reagent for measuring protein such as BCA Protein Assay Reagent Kit (Pierce Biotechnology, Inc) and Protein Assay Kit (BIO-RAD, Inc).

Next, conversion of proMMP-7 into MMP-7 is carried out. A method for conversion includes heating a solution containing proMMP-7 at 37° C. in the presence of 1 mM (4-aminophenyl)mercuric acetate (APMA) or 0.2 µM trypsin or heating a solution containing proMMP-7 at 53° C. (Crabbe et al., Biochemistry, 1992, vol. 31, 8500-8507), any of which method may be used. At this time, 30 to 200 mM sodium chloride may optionally be added (Crabbe et al., Biochemistry, 1992, vol. 31, 8500-8507, WO 2010/047347 A1). Heating time is in a range of 1 to 5 hours and is suitably adjusted depending on a concentration and an amount to be treated of a reagent and proMMP-7. For trypsin, one treated with N-tosyl-L-phenylalanine chloromethyl ketone (TPCK) may be used.

For measurement of an enzymatic activity of MMP-7, cleavage of a fluorescent substrate (Dnp-Pro-Leu-Gly-Leu-Trp-Ala-D-Arg-NH$_2$; SEQ ID NO: 7) by MMP-7 may be measured with a fluorescence measurement apparatus (Crabbe et al., Biochemistry, 1992, vol. 31, 8500-8507). Practically, Kit for measuring MMP-7 activity (ANASPEC) based on the above principle is commercially available. Thus, the activity may be measured using this kit in accordance with protocol attached thereto. For isolation and purification of MMP-7 converted from proMMP-7, the protein purification procedures as described above may be used.

MMP-7 as converted forms aggregates in a solution containing a high concentration of a salt. This more likely occurs in case that a concentration of MMP-7 in a solution is 1 mg/ml or more. The presence of MMP-7 aggregates leads to the decrease in productivity and quality when MMP-7 is manufactured and is made to MMP-7 preparation. As described above, MMP-7 aggregates are monomerized and MMP-7 monomers are maintained in a solution for monomerization containing a monovalent cation compound at 130 mM or less in the presence of calcium chloride. However, in the solution containing a monovalent cation compound at a concentration of more than 130 mM, it is suggested that the possibility to form MMP-7 aggregates is high. Therefore, a method for monomerization of the present invention is incorporated after treatment with a monovalent cation compound at 130 mM or more. More specifically, it is incorporated immediately after conversion of proMMP-7 into MMP-7 by self-activation.

The treatment by a method for monomerization of the present invention is preferably done to MMP-7 at 20 mg/ml or less. When MMP-7 at 20 mg/ml or more is treated, however, as described above, the same suppressive effect to MMP-7 aggregate formation can be expected by adjusting a concentration of calcium chloride.

A solution containing the thus prepared MMP-7 monomers, after the steps of purification and concentration of MMP-7 by ultrafiltration membrane as necessary, is used as a starting material for producing MMP-7 preparation. In the steps as well, a solution for monomerization of the present invention may be used. Once MMP-7 is monomerized, MMP-7 monomers are maintained as far as they are present in a solution for monomerization and the decrease of the enzymatic activity is not observed for a long period of time. Thus, a solution for monomerization of the present invention may be used for preservation of MMP-7 before production of MMP-7 preparation and for the manufacture of a (pharmaceutical) composition comprising MMP-7 as an active ingredient to thereby allow for maintenance of MMP-7 of high quality.

In a method for monomerization of MMP-7 aggregates and a process for preparing MMP-7 which involves said method for monomerization of the present invention, sugar alcohols and sugars exert the suppressive effect to adsorption of MMP-7 to gel widely used in the manufacture of MMP-7 and the suppressive effect to adsorption of MMP-7 to the wall of a vial used for the production of MMP-7 preparation. Such sugar alcohols and sugars include sucrose, lactose, maltose, xylose, trehalose, mannitol, sorbitol, xylitol, maltitol, lactitol, oligosaccharide alcohols, and the like, preferably mannitol and sucrose, and most preferably mannitol.

In case that a low concentration (e.g. 1 µg/ml to 1 mg/ml) of MMP-7 is made to MMP-7 preparation, the loss of MMP-7 due to its adsorption to the wall of a vial is envisaged and thus it is particularly effective that a solution for monomerization contains sugar alcohols and sugars as described above. In case of MMP-7, sugar alcohols or sugars are added at 2% or more where the suppressive effect to adsorption to the wall of a vial is exerted or at 2 to 7% where an osmotic pressure in the body can be adjusted. In accordance with the present invention, a solution for monomerization is used which contains 2 to 5% mannitol or 2 to 7% sucrose where the activity of MMP-7 can be maintained. More preferably, a solution for monomerization is used which consists of 5 to 25 mM Tris buffer (pH 6 to 8) containing 2 to 5% mannitol, 30 to 40 mM sodium chloride and 5 to 30 mM calcium chloride.

MMP-7 dissolved in said solution for monomerization can be used as it is as a (pharmaceutical) composition comprising MMP-7 of the present invention. A (pharmaceutical) composition comprising MMP-7 preferably comprises 2% or more sugar alcohols and/or sugars and a monovalent cation compound (sodium chloride or calcium chloride) at 30 to 40 mM in view of suppression to MMP-7 aggregate formation, maintenance of the activity of MMP-7, suppression to adsorption of MMP-7 to a container, and ensuring quality as an aqueous pharmaceutical composition. More specifically, in case that a concentration of MMP-7 is 20 mg/ml or less, a (pharmaceutical) composition comprising MMP-7 of the present invention preferably comprises 2 to 5% mannitol or 2 to 7% sucrose, 30 to 40 mM sodium chloride and 5 to 30 mM calcium chloride. A (pharmaceutical) composition comprising MMP-7 of the present invention can be stored in liquid, lyophilized or frozen form. In doing so, in order to maintain safety and isotonicity as a medicine, a (pharmaceutical) composition comprising MMP-7 is further added with a compound that is admitted for administration to humans and other animals such as a stabilizing agent, isotonizing agent and a preservative. A (pharmaceutical) composition comprising MMP-7 of the present invention may encompass a solid composition which can be dissolved in a solvent and the composition upon dissolution is the liquid (pharmaceutical) composition comprising MMP-7 of the present invention as described above. A solid composition is obtained by removing a solvent from a liquid (pharmaceutical) composition comprising MMP-7 of the present invention by lyophilization. A solvent is one defined as a solvent in Dictionary of Pharmaceutical Excipients and includes water, ethanol and the like The thus obtained (pharmaceutical) composition comprising MMP-7 of the present invention has a specific enzymatic activity of MMP-7 with suppression of MMP-7 aggregate formation and suppression of adsorption and can be used as a medicament for treating or diagnosing intervertebral disk displacement.

The present invention is further explained in more detail by means of the following Examples but is not construed to be limited thereto.

PREPARATION EXAMPLE (1) Construction of proMMP-7 Expression Vector (pET-MMP7) with APSP Using primers P1 (SEQ ID NO: 1) and P2 (SEQ ID NO: 2), proMMP-7 gene in kidney cDNA library (HumanMTC Panel I, Catalog #: K1420-1 BD) was amplified by PCR. The amplified DNAs were inserted into a cloning vector (pCRII-TOPO, Invitrogen) and the nucleotide sequences of the obtained DNAs were determined. The determination of the nucleotide sequences was carried out with a DNA sequencer. Homology search between the determined nucleotide sequences and the nucleotide sequence of proMMP-7 registered in database (Accession Numbers: NM002423) was carried out to give a plasmid (pCRproMMP-7) where proMMP-7 gene was inserted.

Next, using pCRproMMP-7 as a template and primer P3 (SEQ ID NO: 3), which consists of a restriction enzyme NdeI recognition sequence, a nucleotide sequence coding for PhoA-alkaline phosphatase signal peptide (APSP) sequence and the N-terminal sequence of proMMP-7, and primer P4 (SEQ ID NO: 4), which consists of a restriction enzyme BamHI recognition sequence and the C-terminal sequence of proMMP-7, PCR was performed. The DNAs amplified in the same manner as above were inserted into a cloning vector and the nucleotide sequences of the obtained DNAs were determined. After confirming that no change in the nucleotide sequence occurred, the obtained plasmid was cleaved with restriction enzymes NdeI and BamHI and the obtained fragment was inserted into an expression vector pET22b (Merck, product cord; 69744-3) previously cleaved with the same restriction enzymes to give a plasmid (pET-MMP7) where proMMP-7 gene was inserted.

(2) Construction of Expression Vector pETMMP7 (L13P-A21E) with Modified APSP and Expression Using GeneTailor Site-Directed Mutagenesis System (Invitrogen) in accordance with protocol attached thereto, mutation was introduced into a signal peptidase recognition sequence of APSP sequence (Met-Lys-Gin-Ser-Thr-Ile-Ala-Leu-Ala-Leu-Leu-Pro-Leu-Leu-Phe-Thr-Pro-Val-Thr-Lys-Ala; SEQ ID NO: 8) in pETMMP7 obtained in (1) above [leucine (Leu) at position 13 of the amino acid sequence of APSP was replaced with proline (Pro) and alanine (Ala) at position 21 was replaced with glutamic acid (Glu)]. For modification of APSP, the sequences of M2 (SEQ ID NO: 5) as a 5' primer and P6 (SEQ ID NO: 6) as a 3' primer were used. E. coli was transformed with the obtained pETMMP7 (L13P-A21E) with modified APSP to give a recombinant E. coli (MMP7L13P-A21E) expressing proMMP-7.

Induction of expression was carried out with Overnight Express Autoinduction System 1 (Merck; product cord 71300-3) in accordance with protocol attached thereto. In brief, each colony was suspended in 50 mL LB medium containing 50 µg/mL Ampicillin (Wako Pure Chemical Industries, Ltd.) in 125 mL Erlenmeyer flask, the reagents of Kit were added and the flask was incubated at 37° C. for 16 hours. OD 600 nm of the cell suspension was measured and the cells corresponding to OD 600 nm=20, 1 mL were collected in precipitates by centrifuge. The precipitates were disrupted with 200 µL BugBuster and centrifuged to give precipitates. The precipitates were solubilized with Sample Buffer for SDS-polyacrylamide gel electrophoresis (SDS-PAGE), subjected to 15% acrylamide gel SDS-PAGE and CBB staining was done. As a result, the increase in an expression level of proMMP-7 and the enhancement of the suppressive effects to decomposition were confirmed.

In this Preparation Example, the primers with the following sequences were used.

P1: ccataggtcc aagaacaatt gtctctg (SEQ ID NO: 1)
P2: caatccaatg aatgaatgaa tggatg (SEQ ID NO: 2)
P3: catatgaaac aaagcactat tgcactggca ctcttaccgt tactgtttac ccctgtgacc aaggccctgc cgctgcctca g (SEQ ID NO: 3)
P4: ggatccctat ttctttcttg aattac (SEQ ID NO: 4)
M2: ctgtttaccc ctgtgaccaa ggaactgccg ctgcc (SEQ ID NO: 5)
P6: cttggtcaca ggggtaaaca gtggcggtaa gag (SEQ ID NO: 6)

EXAMPLE 1

Suppressive Effect to MMP-7 Aggregate Formation by Monovalent Cation Chloride (1) Manufacture of MMP-7

E. coli (MMP7L13P-A21E) expressing proMMP-7 obtained by the procedures described in Preparation Example was cultured and propagated as a seed in a glucose medium and induction of proMMP-7 expression was performed with isopropyl-β-thiogalactopyranoside (IPTG). The cells were recovered from the culture solution and disrupted with French press. The solution obtained after disruption of cells was centrifuged and inclusion bodies were recovered in precipitates. Next, the inclusion bodies were dissolved in 6M guanidine hydrochloride containing 0.1 M Tris-HCl (pH 7.5) and 0.1 M dithiothreitol and refolded with 50 mM HEPES buffer (pH 7.5) containing 0.1 mM zinc acetate, 10 mM calcium chloride, 0.2 M sodium chloride and 1.0% Brij 35. Thereafter, proMMP-7 was purified by ion exchange chromatography and hydrophobic chromatography in an ordinary manner. The obtained proMMP-7 was heated at 47° to 48° C. for self-activation to give MMP-7. The obtained MMP-7 was subject to repetition of dilution and concentration with ultrafiltration membrane using 5 mM Tris buffer (pH 7) containing 40 mM NaCl, 10 mM $CaCl_2$ and 3.5% mannitol and stored at −80° C.

(2) Measurement of MMP-7 Aggregates

The solution containing a high concentration of MMP-7 obtained in (1) above was diluted with an aqueous solution containing 5 mM calcium chloride ($CaCl_2$) in which sodium chloride (NaCl) or potassium chloride (KCl) was dissolved to prepare Sample 1 and Sample 2.

Sample 1: 1 mg/ml MMP-7/5 mM $CaCl_2$/each concentration of NaCl (10 to 160 mM)
Sample 2: 1 mg/ml MMP-7/5 mM $CaCl_2$/each concentration of KCl (10 to 160 mM)

Using each 100 µl of the above samples, the effect of sodium chloride and potassium chloride on the formation of MMP-7 aggregates was investigated by dynamic light scattering (device; Wyatt Technology DynaPro (Protein Solutions) Titan, cell; Wyatt Technology 12 uL Cell 8.5 mm Centre Height, temperature; 20° C.). A molecular weight of MMP-7 in each sample was measured and analyzed. MMP-7 with a molecular weight of 38 kDa or less was determined to be monomeric based on the molecular weight of MMP-7 monomers (about 19 kDa). As a result, a molecular weight of MMP-7 in 10 mM to 80 mM NaCl solution was 20 to 29 kDa to reveal that MMP-7 was present as a monomer. Likewise, when potassium chloride was used, the results were obtained that MMP-7 was present as a monomer in 10 mM to 80 mM KCl solution (FIG. 1). The dotted line in the figure shows a molecular weight of 38 kDa.

EXAMPLE 2

Effect of Calcium Chloride on Suppression to MMP-7 Aggregate Formation

The MMP-7 solution obtained in Example 1-(1) was diluted with an aqueous solution in which calcium chloride and sodium chloride were dissolved to prepare Sample 3.
Sample 3: 1 mg/ml MMP-7/each concentration of $CaCl_2$ (0 to 30 mM)/each concentration of NaCl (0 to 160 mM)

The effect of the presence of each concentration of calcium chloride on suppression to MMP-7 aggregate formation was investigated as described in Example 1-(2).

Figure 2:
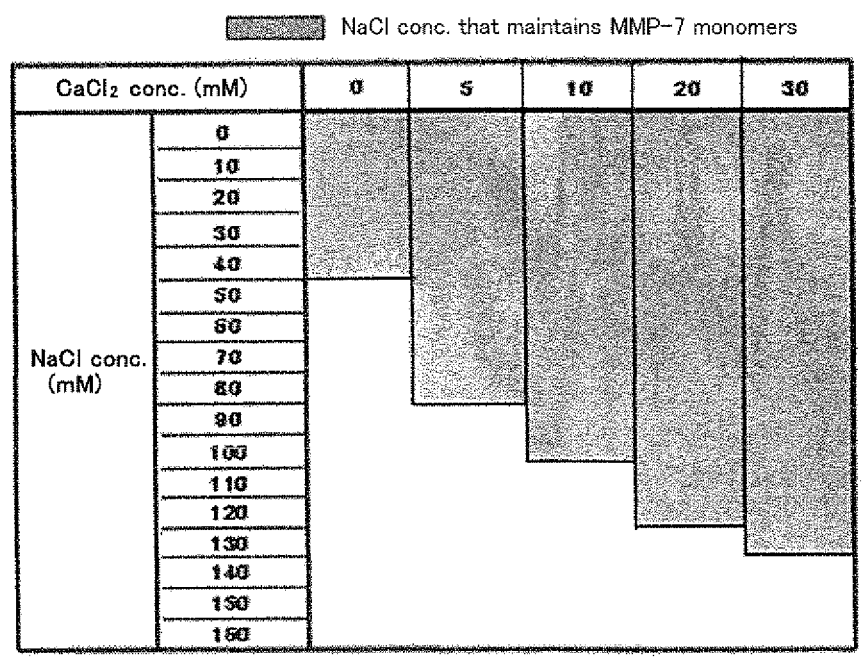
FIG. 2 shows the effects of calcium chloride ($CaCl_2$) on suppression to MMP-7 aggregate formation based on the analysis of molecular weight of MMP-7 measured by dynamic light scattering.

As a result, it was shown that MMP-7 monomer was formed with 40 mM or less NaCl in case of 0 mM $CaCl_2$, with 80 mM or less NaCl in case of 5 mM $CaCl_2$, with 100 mM or less NaCl in case of 10 mM $CaCl_2$, with 120 mM or less NaCl in case of 20 mM $CaCl_2$, and with 130 mM or less NaCl in case of 30 mM $CaCl_2$. Besides, also in case of dilution with water alone, the formation of MMP-7 monomer was observed. Thus, it was revealed that MMP-7 aggregates were formed in the presence of 130 mM or more NaCl but the coexistence of 30 mM or less (up to 30 mM) $CaCl_2$ suppressed the formation of MMP-7 aggregates. Namely, this concentration of calcium chloride has the effect of maintaining and stabilizing MMP-7 monomers more effectively (FIG. 2).

EXAMPLE 3

Effect of Concentration of MMP-7 on MMP-7 Aggregate Formation

The MMP-7 solution obtained in Example 1-(1) was diluted with a solution containing 10 mM $CaCl_2$ and each concentration of sodium chloride to prepare Sample 4 containing each concentration of MMP-7.
Sample 4: each concentration of MMP-7 (10, 15, 20 mg/ml)/ 10 mM $CaCl_2$/each concentration of NaCl (50 to 250 mM)

The effect of a concentration of MMP-7 on the suppressive effect to MMP-7 aggregate formation was investigated by size exclusion chromatography (HPLC device; HEWLETT PACKED 1100 series, carrier; TOYOPARL HW50S, temperature; 25° C., flow rate 0.5 mL/min, wavelength 280 nm). A column size was 5 mm diameter and 150 mm length and equilibration of column was conducted with a solution containing 5 mM Tris-HCl (pH 7), 10 mM $CaCl_2$, 3.5% mannitol and 40 to 500 mM NaCl.

Under these conditions, proteins with a molecular weight 60 kDa to 80 kDa appear in void volume (1.8 minutes after initiation of chromatography). Thus, a peak in the vicinity of 2 minutes after initiation of chromatography (or leading peak) was considered to be MMP-7 aggregates and, using an area of the peak as an index, a concentration of sodium chloride with which MMP-7 aggregates were formed were calculated.

Figure 3:
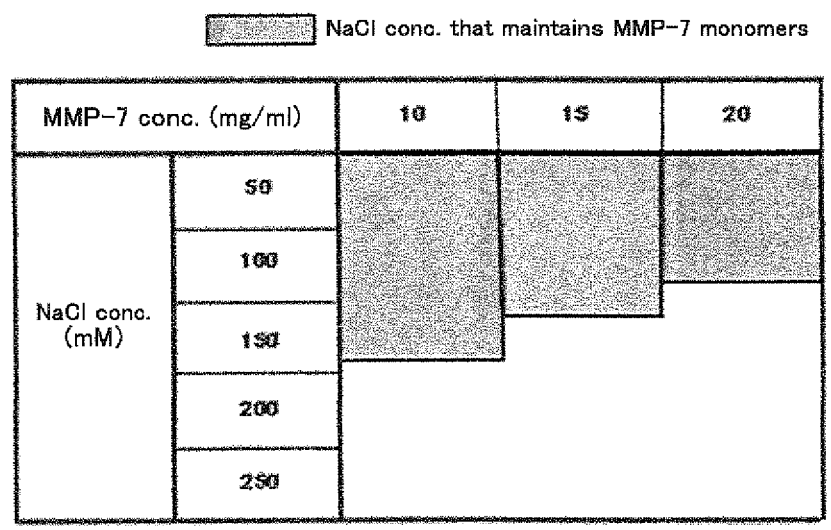
FIG. 3 shows the effects of a concentration of MMP-7 on MMP-7 aggregate formation based on the analysis of molecular weight of MMP-7 measured by size exclusion chromatography.

As a result, it was found that, although the suppressive effect of sodium chloride to MMP-7 aggregate formation got weakened depending on a concentration of MMP-7, MMP-7 was present as monomers with 0 to 80 mM NaCl in case of MMP-7 at 20 mg/ml or less (FIG. 3). From the results of Example 2 (FIG. 2), it is evident that a concentration of sodium chloride with which MMP-7 monomers are maintained increases proportionally with the increase of a concentration of calcium chloride. In the present Example, if 30 mM $CaCl_2$ is used, it is assumed that MMP-7 at 20 mg/ml exists as monomers even in the presence of 100 mM NaCl. Besides, when MMP-7 at more than 20 mg/ml is used, it is assumed that MMP-7 can be maintained as monomers by increasing a concentration of calcium chloride.

The same experiment as above was conducted after Sample 4 was left to stand at 4° C. overnight to give the same results as in FIG. 3.

EXAMPLE 4

Effect of MMP-7 Aggregate Formation on Enzymatic Activity

The MMP-7 solution obtained in Example 1-(1) was diluted with 5 mM Tris buffer (pH 7) containing 40 mM NaCl and 10 mM $CaCl_2$ to prepare Sample 5 containing each concentration of MMP-7.
Sample 5: each concentration of MMP-7 (0.1, 2, 20 mg/ml)/ 10 mM $CaCl_2$/40 mM NaCl/5 mM Tris buffer (pH7)

The solutions containing each concentration of MMP-7 were diluted to 0.1 mg/ml with 50 mM Tris buffer (pH 7) containing 150 mM NaCl and 10 mM $CaCl_2$ or 10 mM Tris buffer (pH 7) containing 40 mM NaCl and 10 mM $CaCl_2$ (primary dilution) and further diluted to 5 ng/ml with 50 mM Tris buffer (pH 7) containing 150 mM NaCl and 10 mM $CaCl_2$ (secondary dilution). For the resulting dilutions, a cleavage activity to a fluorescent substrate (Dnp-Pro-Leu-Gly-Leu-Trp-Ala-D-Arg-$NH_2$; SEQ ID NO: 7) was measured using Kit for measuring MMP-7 activity (ANASPEC) in accordance with protocol attached thereto.

Figure 4:
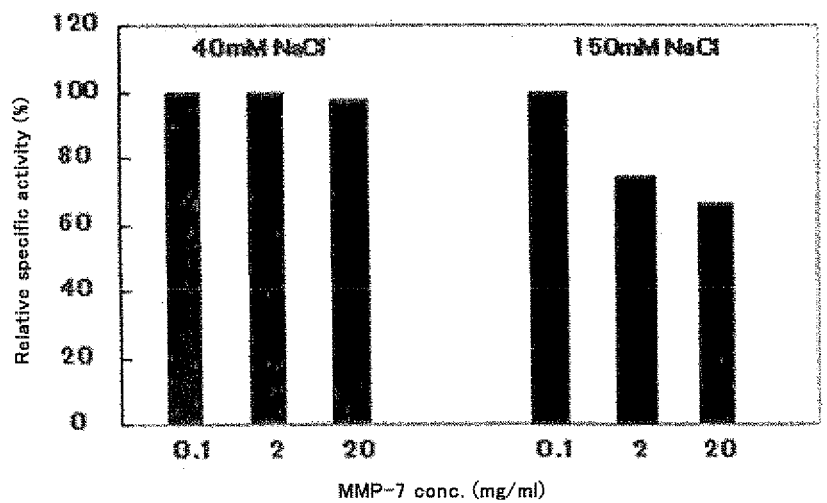
FIG. 4 shows the effects of sodium chloride (NaCl) on the enzymatic activity of MMP-7 when MMP-7 at 0.1 mg/ml, 2 mg/ml or 20 mg/ml is diluted with a Tris buffer containing 150 mM NaCl or 40 mM NaCl.

As a result, the enzymatic activity was decreased for MMP-7 at 2 mg/ml or more diluted with Tris buffer (pH7) containing 150 mM NaCl in the primary dilution (FIG. 4). This decrease in the enzymatic activity is consistent with MMP-7 aggregate formation. On the other hand, at a concentration of 0.1 mg/ml or less, the decrease in the enzymatic activity was not observed, suggesting that aggregate formation by 150 mM NaCl did not occur at this concentration of MMP-7.

EXAMPLE 5

Effect of Concentration of Sodium Chloride on Step of Concentration of MMP-7 by Ultrafiltration Membrane The MMP-7 solution obtained in Example 1-(1) was diluted with 5 mM Tris buffer (pH 7) containing 10 mM $CaCl_2$ to prepare Sample 6 containing each concentration of sodium chloride.
Sample 6: 4 mg/ml MMP-7/10 mM $CaCl_2$/each concentration of NaCl (40 mM, 80 mM, 200 mM, 500 mM)/5 mM Tris buffer (pH 7)

Each 4 ml of Sample 6 was concentrated with centrifuge (2500 g) using ultrafiltration membrane (Amicon Ultra-4 10K) and a volume of filtrate and absorbance of the concentrate at a constant time interval.

As a result, MMP-7 could be concentrated in a shorter time when a lower concentration of sodium chloride was used whereas it took a longer time for concentration when a higher concentration of sodium chloride was used (Table 1). In Table 1, the symbol (-) denotes the termination of concentration.

TABLE 1

Permeation rate of centrifuge filtrate (%: filtrate/total amount)

| | Time of centrifuge (min.) | | | | | | |
|---|---|---|---|---|---|---|---|
| | 10 | 15 | 18 | 23 | 33 | 50 | 64 |
| 40 mM NaCl (%) | 87.5 | 95 | — | — | — | — | — |
| 80 mM NaCl (%) | 75 | 87.5 | 87.5 | 95 | — | — | — |
| 0.2M NaCl (%) | 40 | 55 | 65 | 72.5 | 82.5 | 92.5 | — |
| 0.5M NaCl (%) | 32.5 | 45 | 50 | 55 | 65 | 75 | 82.5 |

EXAMPLE 6

Suppressive Effect of Mannitol on Adsorption of MMP-7
(1) Suppression to Adsorption of MMP-7 to Gel The MMP-7 solution obtained in Example 1-(1) was diluted with 5 mM Tris buffer (pH 7) containing 10 mM $CaCl_2$ and 40 mM NaCl to prepare Sample 7.
Sample 7: 5.5 mg/ml MMP-7/10 mM $CaCl_2$/40 mM NaCl Sample 7 (1 ml) was applied to a column (HW40F, 26×6 cm, Tosoh Corporation) previously equilibrated with 5 mM Tris buffer (pH 7) containing 10 mM $CaCl_2$ and 40 mM NaCl, and after washing with the Tris buffer, eluted with the Tris buffer containing 3.5% mannitol (flow rate: 5 ml/min).

Figure 5:
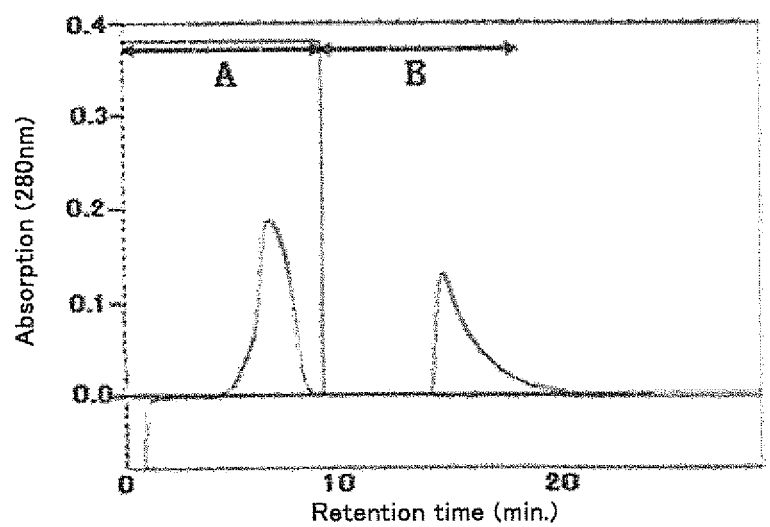
FIG. 5 shows the suppressive effects of mannitol to adsorption of MMP-7 to gel. A: 5 mM Tris buffer (pH 7)/10 mM $CaCl_2$/40 mM NaCl; B: 5 mM Tris buffer (pH 7)/10 mM $CaCl_2$/40 mM NaCl/3.5% mannitol

As a result, MMP-7 adsorbed to gel was eluted by mannitol (FIG. 5). This result suggests that mannitol has a suppressive effect to adsorption of MMP-7 to gel.

(2) Suppression to Adsorption of MMP-7 to Wall of Container

The MMP-7 solution obtained in Example 1-(1) was diluted with 5 mM Tris buffer (pH 7) containing 10 mM $CaCl_2$, 40 mM NaCl and mannitol or sucrose to prepare solutions (1 ml) of Samples 8 to 10 in vials. The concentrations were adjusted so that each Sample has the same osmotic pressure. A control was the MMP-7 solution diluted with the Tris buffer not containing mannitol and sucrose (Sample 10).
Sample 8: 50 μg/ml MMP-7/10 mM $CaCl_2$/40 mM NaCl/5 mM Tris buffer (pH 7)/3.5% mannitol
Sample 9: 50 μg/ml MMP-7/10 mM $CaCl_2$/40 mM NaCl/5 mM Tris buffer (pH 7)/6.6% sucrose
Sample 10: 50 μg/ml MMP-7/10 mM $CaCl_2$/40 mM NaCl/5 mM Tris buffer (pH 7)

After left to stand at room temperature for 3 hours, each solution in vials was diluted in two steps. For primary dilution, 5 mM Tris buffer (pH 7) containing 10 mM $CaCl_2$ and 40 mM NaCl was used. For secondary dilution, 1% Block Ace (Block Ace powder: DS Pharma Biomedical)/TBS-T (0.05% Tween20/50 mM Tris/150 mM NaCl) was used. MMP-7 in the solution was quantitated by ELISA. For ELISA, rabbit anti-MMP-7 antibody obtained by immunizing rabbit with MMP-7, biotin-labeled rabbit anti-MMP-7 antibody wherein the rabbit anti-MMP-7 antibody was labeled with biotin labelling reagent (Biotin (Long Arm) NHS-Water Soluble: Vector Laboratories), Horseradish Peroxidase (HRP)-labeled Streptavidin (Horseradish Peroxidase Streptavidin Concentrate: Vector Laboratories) and HRP substrate solution (Peroxidase Substrate Solution B: KPL). As a control for ELISA reaction, MMP-7 standard for ELISA with a fixed concentration of MMP-7 was used. A concentration of MMP-7 was calculated by measuring absorption.

Figure 6:
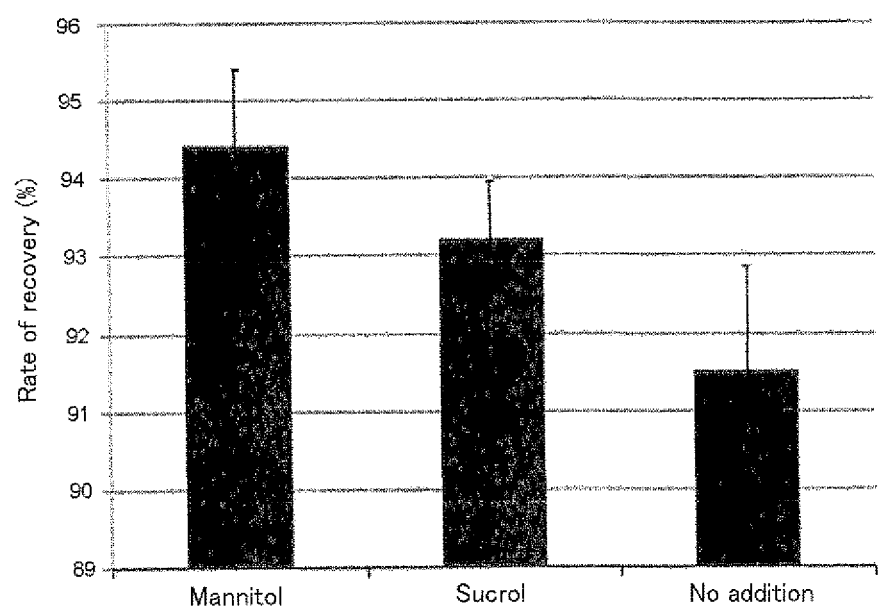
FIG. 6 shows the suppressive effects of mannitol and sucrose to adsorption of MMP-7 to the wall of a vial.

As a result, as compared to no addition (Sample 10), a higher rate of recovery of MMP-7 was shown when mannitol (Sample 8) or sucrose (Sample 9) was added to confirm the suppressive effect thereof (FIG. 6).

Next, an effective concentration of mannitol or sucrose for suppression to absorption of MMP-7 to the wall of a container and effect of mannitol or sucrose on the enzymatic activity of MMP-7 was investigated. The MMP-7 solution obtained in Example 1-(1) was diluted with 5 mM Tris buffer (pH 7) containing 10 mM $CaCl_2$, 40 mM NaCl and mannitol or sucrose to prepare solutions (1 ml) of Samples 12 to 16 in vials. A control was the MMP-7 solution diluted with the Tris buffer not containing mannitol and sucrose (Sample 11).
Sample 11: 50 μg/ml MMP-7/10 mM $CaCl_2$/40 mM NaCl/5 mM Tris buffer (pH 7)
Sample 12: 50 μg/ml MMP-7/10 mM $CaCl_2$/40 mM NaCl/5 mM Tris buffer (pH7)/1% mannitol
Sample 13: 50 μg/ml MMP-7/10 mM $CaCl_2$/40 mM NaCl/5 mM Tris buffer (pH7)/2% mannitol
Sample 14: 50 μg/ml MMP-7/10 mM $CaCl_2$/40 mM NaCl/5 mM Tris buffer (pH7)/2% sucrose
Sample 15: 50 μg/ml MMP-7/10 mM $CaCl_2$/40 mM NaCl/5 mM Tris buffer (pH7)/5% mannitol
Sample 16: 50 μg/ml MMP-7/10 mM $CaCl_2$/40 mM NaCl/5 mM Tris buffer (pH7)/7% sucrose After left to stand at room temperature for 3 hours, each solution in vials was diluted in two steps. Each solution in vials was diluted with primary dilution solution of 50 mM Tris buffer (pH 7) containing 0.01% Briji35, 0.01% BSA, 150 mM NaCl and 10 mM $CaCl_2$ to 5 ng/ml and the cleavage activity to a fluorescent substrate (the enzymatic activity of MMP-7) was measured as in Example 4. In this experiment, a fluorescent substrate obtained from PEPTIDE INSTITUTE, INC. (MOCAc-Pro-Leu-Gly-Leu-$A_2$pr(Dnp)-Ala-Arg-$NH_2$; (7-Methoxycoumarin-4-yl)acetyl-L-prolyl-L-leucylglycyl-L-leucyl-[$N^β$-(2,4-dinitrophenyl)-L-2,3-diaminopropionyl]-L-alanyl-L-arginine amide; SEQ ID NO: 9) was used. For secondary dilution, 1% Block Ace (Block Ace powder: DS Pharma Biomedical)/TBS-T (0.05% Tween20/50 mM Tris/150 mM NaCl) was used and a concentration of MMP-7 in the solution was measured by ELISA as above.

Figure 7:
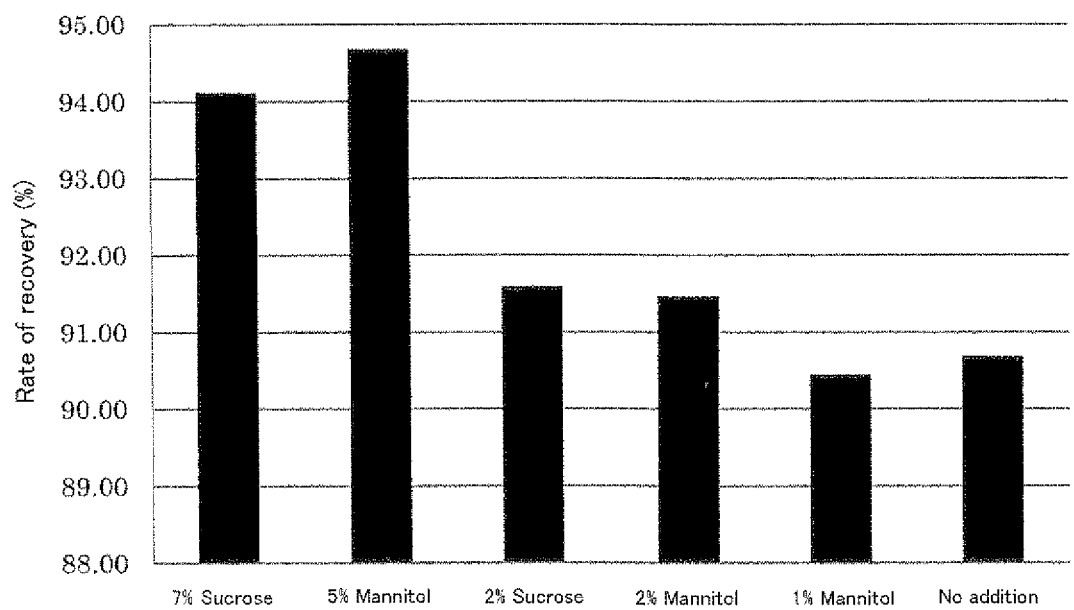
FIG. 7 shows the suppressive effects of mannitol and sucrose at each concentration to adsorption of MMP-7 to the wall of a vial.
Figure 8:
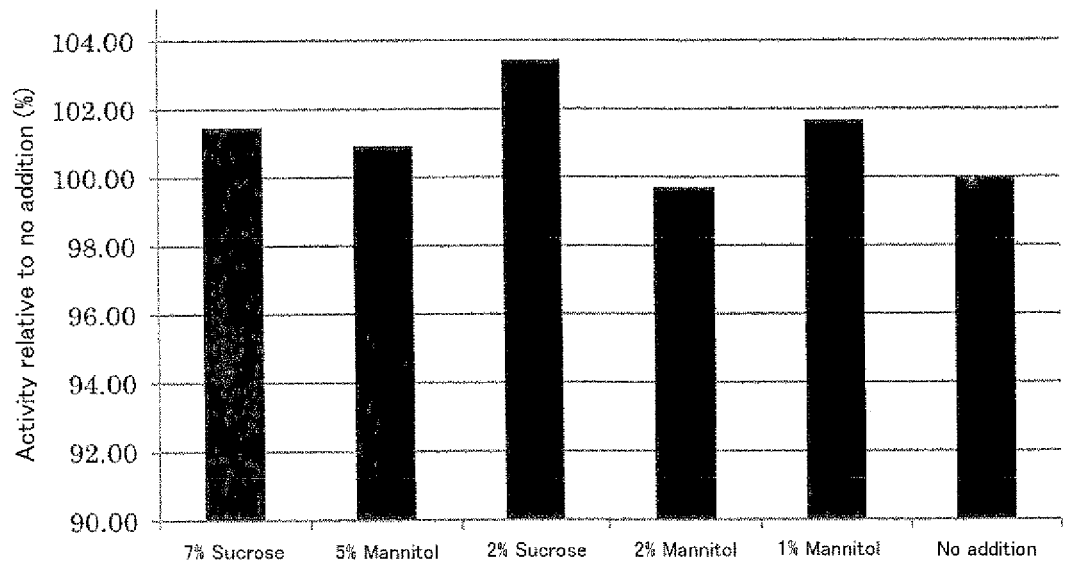
FIG. 8 shows the effects of mannitol and sucrose at each concentration on the enzymatic activity of MMP-7.

As a result, as compared to no addition (Sample 11), a higher rate of recovery of MMP-7 was shown when 2 to 5% mannitol (Samples 13, 15) or 2 to 7% sucrose (Samples 14, 15) was added to confirm the suppressive effect thereof to adsorption to the wall of a container (FIG. 7). No decrease in the enzymatic activity of MMP-7 was observed after addition of mannitol or sucrose (FIG. 8).

EXAMPLE 7

Effect of Mannitol on Suppression to MMP-7 Aggregate Formation

The MMP-7 solution obtained in Example 1-(1) was subject to buffer exchange with 5 mM Tris buffer (pH 7) containing each concentration of NaCl, 5 mM $CaCl_2$ and 3.5% mannitol using spin filter and then was diluted with the Tris buffer to prepare Samples 17 to 22. A control was the MMP-7 solution treated with the Tris buffer not containing mannitol (Sample 17).

Figure 9:
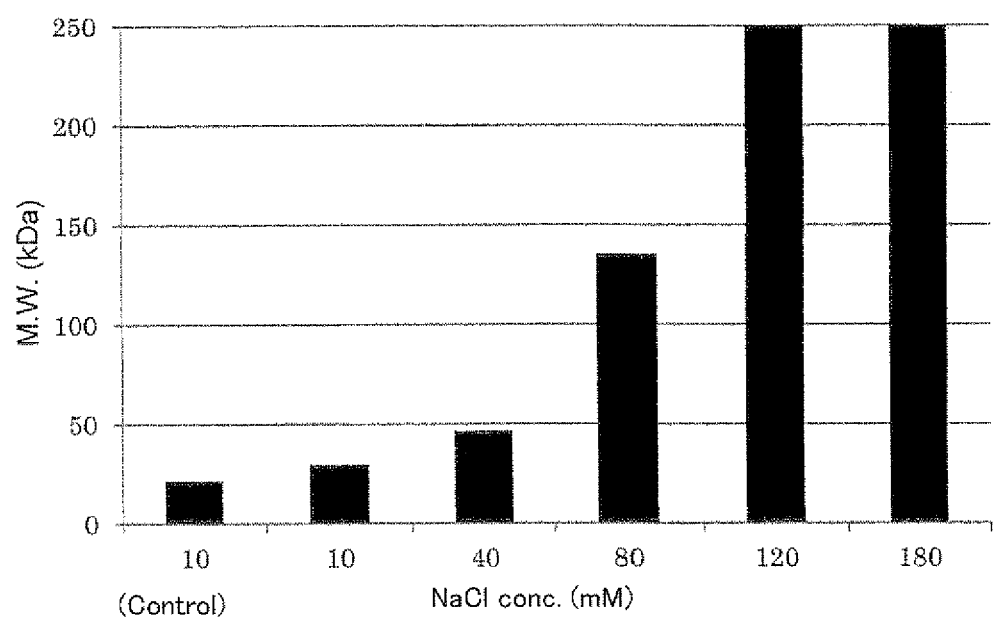
FIG. 9 shows the effects of mannitol on suppression to MMP-7 aggregate formation.

Sample 17: 10 mM NaCl/1 mg/ml MMP-7/5 mM CaCl$_2$
Sample 18: 10 mM NaCl/1 mg/ml MMP-7/5 mM CaCl$_2$/ 3.5% mannitol
Sample 19: 40 mM NaCl/1 mg/ml MMP-7/5 mM CaCl$_2$/ 3.5% mannitol
Sample 20: 80 mM NaCl/1 mg/ml MMP-7/5 mM CaCl$_2$/ 3.5% mannitol
Sample 21: 120 mM NaCl/1 mg/ml MMP-7/5 mM CaCl$_2$/ 3.5% mannitol
Sample 22: 180 mM NaCl/1 mg/ml MMP-7/5 mM CaCl$_2$/ 3.5% mannitol A molecular weight of MMP-7 in each Sample was measured by dynamic light scattering as described in Example 1-(2). As a result, it was shown that MMP-7 formed aggregates with 40 mM or more sodium chloride (FIG. 9).

INDUSTRIAL APPLICABILITY

A method for monomerizing MMP-7 aggregates of the present invention can be used for the manufacture of MMP-7 and the production of MMP-7 preparation.

The invention claimed is:

1. A method for monomerization of matrix metalloproteinase 7 (MMP-7) aggregates which comprises treating MMP-7 aggregates with a solution comprising a monovalent cation compound at 80 mM or less or with a solution not comprising a monovalent cation compound, wherein MMP-7 monomers are obtained.

2. The method for monomerization according to claim 1 wherein the MMP-7 aggregates are treated with a solution not comprising a monovalent cation compound.

3. The method for monomerization according to claim 1 wherein the monovalent cation compound is at 40 mM or less.

4. The method for monomerization according to claim 1 wherein the monovalent cation compound is selected from the group consisting of sodium chloride, potassium chloride, sodium sulfate, potassium sulfate, sodium carbonate, potassium carbonate, sodium phosphate and potassium phosphate.

5. The method for monomerization according to claim 1 wherein the monovalent cation compound is from a monovalent cation chloride.

6. The method for monomerization according to claim 5 wherein the monovalent cation compound is selected from the group consisting of sodium chloride and potassium chloride.

7. The method for monomerization according to claim 1 wherein the solution further comprises calcium chloride.

8. The method for monomerization according to claim 7 wherein the calcium chloride is at 30 mM or less.

9. The method for monomerization according to claim 1 wherein the solution is a buffer solution.

10. The method for monomerization according to claim 9 wherein the buffer solution is 5 to 25 mM Tris buffer.

11. The method for monomerization according to claim 1 wherein the MMP-7 is at 20 mg/ml or less.

12. The method for monomerization according to claim 10 wherein the solution is 5 to 25 mM Tris buffer having a pH of 6 to 8 comprising 30 to 40 mM sodium chloride and 5 to 30 mM calcium chloride.

13. The method for monomerization according to claim 1 wherein the solution further comprises sugar alcohols and/or sugars.

14. The method for monomerization according to claim 13 wherein the sugar alcohols and/or sugars are selected from the group consisting of sucrose, lactose, maltose, xylose, trehalose, mannitol, sorbitol, xylitol, maltitol, lactitol, and oligosaccharide alcohols.

15. The method for monomerization according to claim 13 wherein the sugar alcohols and/or sugars are at 2 w/v % or more.

16. The method for monomerization according to claim 15 wherein the sugar alcohols and/or sugars are at 2 to 7 w/v %.

17. The method for monomerization according to claim 14 wherein the sugar alcohols and/or sugars are mannitol or sucrose.

18. The method for monomerization according to claim 17 wherein the mannitol is at 2 to 5% and the sucrose is at 2 to 7 w/v %.

19. A process for preparing monomers of MMP-7 comprising the following steps:
    a step of disrupting cells producing proMMP-7 inclusion body;
    a step of dissolution/refolding treatment of proMMP-7 inclusion body;
    a step of purification of proMMP-7;
    a step of self-activation of proMMP-7 into MMP-7; and
    a step comprising treating MMP-7 with a solution comprising a monovalent cation compound at 80 mM or less or with a solution not comprising a monovalent cation compound, wherein MMP-7 monomers are obtained.

20. The process according to claim 19, further comprising a step of concentration using an ultrafiltration membrane.

* * * * *